US011202922B2

(12) United States Patent
Chabrol

(10) Patent No.: US 11,202,922 B2
(45) Date of Patent: Dec. 21, 2021

(54) DEVICE FOR OPTICALLY STIMULATING THE BRAIN VIA AN OPTICAL FIBER

(71) Applicant: Commissariat à l'Energie Atomique et aux Energies Alternatives, Paris (FR)

(72) Inventor: Claude Chabrol, Poisat (FR)

(73) Assignee: Commissariat à l'Energie Atomique et aux Energies Alternatives, Paris (FR)

(*) Notice: Subject to any disclaimer, the term of this patent is extended or adjusted under 35 U.S.C. 154(b) by 117 days.

(21) Appl. No.: 16/063,260

(22) PCT Filed: Dec. 7, 2016

(86) PCT No.: PCT/FR2016/053249
§ 371 (c)(1),
(2) Date: Jun. 16, 2018

(87) PCT Pub. No.: WO2017/103381
PCT Pub. Date: Jun. 22, 2017

(65) Prior Publication Data
US 2018/0369608 A1      Dec. 27, 2018

(30) Foreign Application Priority Data

Dec. 16, 2015   (FR) ...................................... 1562525

(51) Int. Cl.
*A61N 5/00*    (2006.01)
*A61N 5/06*    (2006.01)
*A61N 5/067*   (2006.01)

(52) U.S. Cl.
CPC ......... *A61N 5/0622* (2013.01); *A61N 5/0601* (2013.01); *A61N 5/067* (2021.08);
(Continued)

(58) Field of Classification Search
CPC .... A61N 5/06; A61N 2005/06; A61N 5/0622; A61N 5/0601
(Continued)

(56) References Cited

U.S. PATENT DOCUMENTS 5,036,201 A * 7/1991 Carroll ................ A61N 5/1014
250/363.1
5,699,142 A * 12/1997 Lee ....................... A61F 2/1618
351/159.11
(Continued)

FOREIGN PATENT DOCUMENTS

EP      0206943 A2    12/1986
FR      3010321 A1     3/2015
(Continued)

OTHER PUBLICATIONS

International Search Report for PCT/FR2016/053249 dated Feb. 20, 2017, 3 pages.
(Continued)

*Primary Examiner* — Gary Jackson
*Assistant Examiner* — Anant A Gupta
(74) *Attorney, Agent, or Firm* — Moreno IP Law LLC

(57) ABSTRACT

The invention relates to a device comprising: a light source mounted in a housing, the housing comprising a transparent window opposite the light source; an optical fiber fitted with a connector suitable for detachably engaging with the housing to retain an input surface of the optical fiber opposite the light source via the window; and an interface element made of transparent elastomeric material suitable, in the connected position, for being retained so as to be compressed between the window and the input surface of the optical fiber.

10 Claims, 3 Drawing Sheets

(52) U.S. Cl.
CPC ............... *A61N 2005/063* (2013.01); *A61N 2005/0612* (2013.01); *A61N 2005/0655* (2013.01); *A61N 2005/0659* (2013.01)

(58) Field of Classification Search
USPC .................................. 606/2–19; 607/88–92
See application file for complete search history.

(56) References Cited

U.S. PATENT DOCUMENTS

| | | | | |
|---|---|---|---|---|
| 6,144,787 | A * | 11/2000 | Johnston | G02B 6/262 |
| | | | | 385/117 |
| 6,501,900 | B1 * | 12/2002 | Aloisio, Jr. | G02B 6/266 |
| | | | | 385/140 |
| 2004/0015211 | A1 | 1/2004 | Nurmikko et al. | |
| 2011/0125077 | A1 * | 5/2011 | Denison | A61N 5/0622 |
| | | | | 604/20 |
| 2012/0330293 | A1 * | 12/2012 | Arai | A61N 5/062 |
| | | | | 606/15 |
| 2017/0139148 | A1 * | 5/2017 | Yamaguchi | G02B 6/3821 |

FOREIGN PATENT DOCUMENTS

| | | | |
|---|---|---|---|
| JP | 2001305394 A | | 10/2001 |
| JP | 2002156563 A | * | 5/2002 |
| JP | 2002156563 A | | 5/2002 |
| JP | 2004252425 A | | 9/2004 |

OTHER PUBLICATIONS

Written Opinion of the International Searching Authority for International Application No. PCT/FR2016/053249, dated Feb. 20, 2017, 5 pages.

* cited by examiner

DEVICE FOR OPTICALLY STIMULATING THE BRAIN VIA AN OPTICAL FIBER

FIELD

The present application generally concerns the field of implantable devices, and more particularly aims at an implantable optical device for the deep stimulation of the human or animal brain by optical irradiation.

BACKGROUND

Deep brain stimulation is a therapeutic technique comprising the implantation in the patient's brain of a device enabling to stimulate specific portions of the brain. Treatments of certain neural dysfunctions, such as Parkinson's disease, by optical irradiation of brain portions with a light source emitting in Infrared, have in particular been provided.

Implantable devices enabling to implement treatments by deep optical stimulation of the brain by means of an optical fiber introduced into the patient's brain, via which light originating from a light source outside of the brain is guided towards the brain, have already been provided. An example of such a device is described in French patent application FR3010321 previously filed by the applicant.

Document US2011/125077 describes another example of a device for the treatment by deep optical stimulation of the brain.

It would however be desirable to be able to at least partly improve certain aspects of known devices of deep optical stimulation of the brain.

SUMMARY

Thus, an embodiment provides a device comprising: a light source assembled in a package, the package comprising a transparent window opposite the light source; an optical fiber fitted with a connector capable of detachably engaging with the package to maintain an input surface of the optical fiber opposite the light source via the window; and an interface element made of a transparent elastomeric material capable, in connected position, of being maintained compressed between the window and the input surface of the optical fiber.

According to an embodiment, opposite the region where it is placed in contact with the input surface of the optical fiber, the interface element has a first thickness in disconnected position and a second thickness in connected position, the first thickness being from 1.1 to 1.3 times greater than the second thickness.

According to an embodiment, in disconnected position, the surface of the interface element intended to be placed in contact with the input surface of the optical fiber is bulged.

According to an embodiment, in disconnected position, the surface of the interface element intended to be placed in contact with the input surface of the optical fiber has nanostructures or microstructures.

According to an embodiment, the interface element is made of silicone or of polyurethane.

According to an embodiment, the light source is a laser source.

According to an embodiment, the window is made of sapphire or of silica.

According to an embodiment, the package is hermetically closed.

According to an embodiment, the device further comprises an optical system capable, in connected position, of focusing the light emitted by the source onto the input surface of the optical fiber.

According to an embodiment, the interface element is rigidly assembled to the package or to the connector.

According to an embodiment, the device further comprises a power supply and control unit coupled to the light source by a connecting cable.

BRIEF DESCRIPTION OF THE DRAWINGS

The foregoing and other features and advantages will be discussed in detail in the following non-limiting description of specific embodiments in connection with the accompanying drawings, among which.

DETAILED DESCRIPTION OF THE PRESENT EMBODIMENTS

Figure 1:
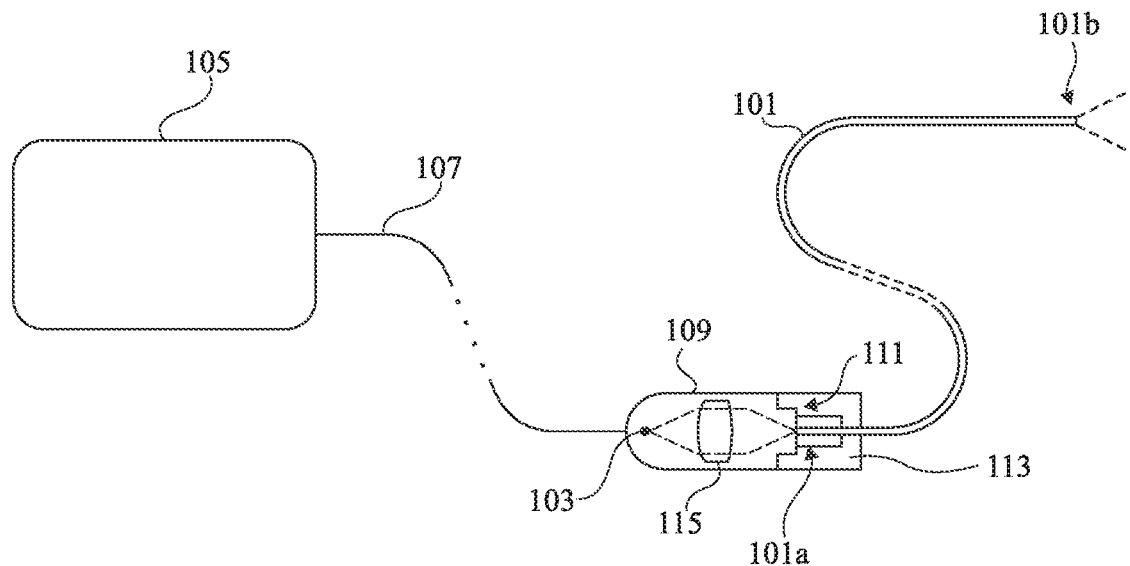
FIG. 1 is a simplified representation of an example of an implantable device for the optical irradiation of the brain.

The same elements have been designated with the same reference numerals in the different drawings and, further, the various drawings are not to scale. For clarity, only those elements which are useful to the understanding of the described embodiments have been shown and are detailed. The terms "approximately", "substantially", and "in the order of" are used herein to designate a tolerance of plus or minus 10%, preferably of plus or minus 5%, of the value in question.

FIG. 1 is a simplified representation of an example of an implantable device for the optical irradiation of the brain. The device comprises an optical fiber 101 having a first end or distal end 101b intended to be implanted inside of the brain opposite a brain portion which is desired to be stimulated. The device of FIG. 1 further comprises a light source 103 coupled to a second end or proximal end 101a of optical fiber 101. The device of FIG. 1 further comprises a unit 105 for powering and controlling light source 103, for example comprising an electric battery and a control circuit capable of controlling light source 103 to implement desired stimulations of the brain. In practice, to minimize risks for the patient, only optical fiber 101 is effectively implanted in the patient's brain, the other elements being maintained outside of the brain for the entire duration of the treatment. Light source 103 and power supply and control unit 105 may for example be implanted in other portions of the patient's body. As an example, light source 103 may be implanted under the patient's scalp or in the patient's skull, and power supply and control unit 105 may be implanted at the level of the patient's thorax. In this case, the device may comprise a connecting cable 107 coupling unit 105 to light source 103. As a variation, light source 103 may be rigidly assembled to power supply and control unit 105.

To perform certain setting or maintenance operations without having to extract optical fiber 101 from the patient's brain, it is important for light source 103 to be detachably or removably coupled to optical fiber 101. To achieve this, source 103 is arranged in a protection package 109, the package comprising a transparent window 111 facing light source 103. Further, the device comprises, on the side of proximal end 101a of optical fiber 101, a connector 113 rigidly assembled to optical fiber 101. Connector 113 is capable of detachably or removably cooperating with package 109 to maintain proximal end 101a of the optical fiber opposite light source 103 through window 111. In the shown example, the device further comprises, inside of package 109, an optical system 115 capable of focusing the light emitted by source 103 onto input surface 101a of optical fiber 101 in the connected position, that is, when connector 113 is connected to package 109. In connected position, the light emitted by light source 103 penetrates into optical fiber 101 through its proximal end 101a, is guided into the brain by optical fiber 101, then comes out of optical fiber 101 through its distal end 101b to illuminate the brain.

A problem which is posed is that of keeping the interface between window 111 of protection package 109 of light source 103 and input surface 101a of optical fiber 101 clean. It must indeed be avoided for impurities to interpose between window 111 and input surface 101a of optical fiber 101, which would degrade the quality of the optical transmission. This problem particularly arises in the case of implantable devices, where physiologic fluid might interpose between window 111 and input surface 101a of optical fiber 101 (during the surgery or due to an infiltration).

Figure 2:
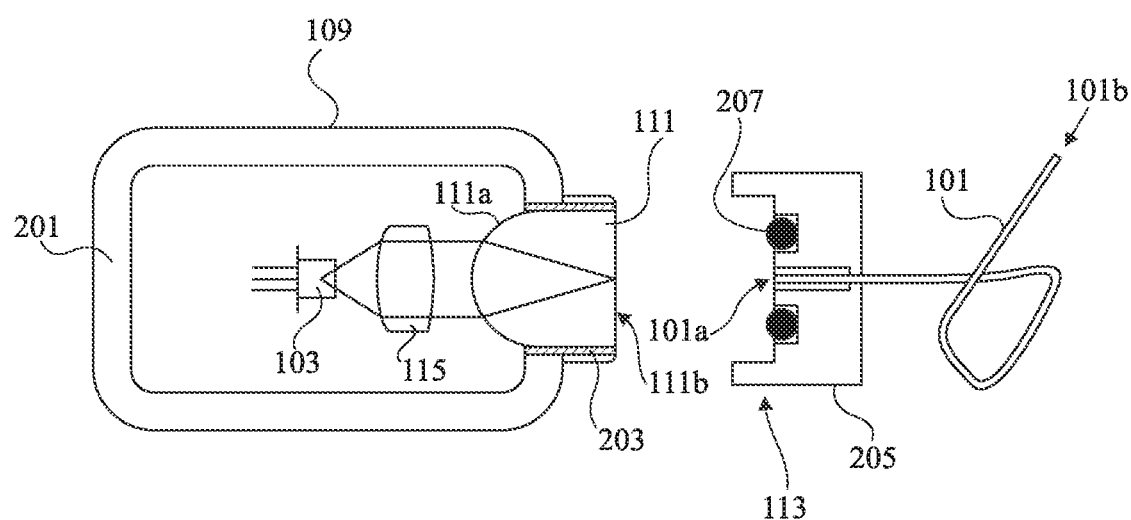
FIG. 2 is a cross-section view illustrating in further detail an example of an implantable device for the optical irradiation of the brain.

FIG. 2 is a cross-section view illustrating in further detail an example of a device of the type described in relation with FIG. 1. For simplification, power supply and control unit 105 and connection 107 between unit 105 and light source 103 have not been shown in FIG. 2. Only light source 103, protection package 109, and its window 111, optical system 115, connector 113, and optical fiber 101 have been shown in FIG. 2.

Light source 103 is for example a laser source. As an example, source 103 is an infrared source, for example, emitting in a waveband in the range from 650 to 1,100 nm. Optical fiber 101 may comprise an outer sheath made of a biocompatible material and, on the side of its distal end 101b and/or on the side of its proximal end 101a, a protection sleeve made of a transparent biocompatible material. Package 109 is for example made of one or a plurality of biocompatible materials. As an example, package 109 comprises a body 201 made of an opaque biocompatible material, for example, titanium, and window 111 may be made of a transparent biocompatible material, for example, sapphire or silica. Package 109 is for example capable of hermetically isolating all the non-biocompatible components that it contains. As an example, package 109 is closed under a neutral atmosphere (oxygen-free), for example, under argon. Window 111 is for example arranged in an opening of body 201, a hermetic biocompatible solder 203, for example, a gold solder, ensuring the hermeticity between the walls of the opening and the window. The electrical feedthroughs (not shown) of package 109, enabling to electrically couple light source 103 to power supply and control unit 105, are for example made of biocompatible materials, for example, iridium-platinum for the conductive portions and ceramic or sapphire for the insulating portions. Such electrical feedthroughs may be closed by hermetic biocompatible solder, for example, by gold solder. Similarly, connector 113 may be made of one or a plurality of biocompatible materials.

Window 111 comprises, on the outer side of package 109, an outer surface or output surface 111b, for example planar. When connector 113 is connected to package 109, output surface 111b of window 111 is in contact with input surface 101a of optical fiber 101. Window 111 further comprises, on the inner side of the package (opposite to surface 111b), an inner surface or input surface 111a. In the example of FIG. 2, input surface 111a of window 111 is convex, so that window 111 behaves as a lens and contributes to the shaping of the beam emitted by source 103. In this example, the optical assembly comprising optical system 115 and window 111 is capable of focusing the light emitted by light source 103 substantially onto output surface 111b of window 111. Window 111 may comprise an antireflection layer on its inner surface 111a.

Connector 113 comprises a body 205, for example, made of titanium, rigidly assembled to a proximal end of optical fiber 101. Input surface 101a of optical fiber 101 is substantially flush with a surface of body 205 placed in contact with outer surface 111a of the window when connector 113 is connected to package 109. For simplification, the elements for locking connector 113 in connected position have not been shown. These elements may for example comprise a screw clamp ring, a bayonet connector, or any other adapted locking mechanism.

To prevent substances capable of degrading the quality of the optical transmission from interposing between output surface 111b of window 111 and input surface 101a of optical fiber 101, the device of FIG. 2 further comprises an O-ring 207 surrounding proximal end 101a of optical fiber 101. In connected position, O-ring 207 is maintained compressed between body 205 of connector 113 and outer surface 111b of the window, to prevent the penetration of unwanted substances into the optical coupling area between window 111 and optical fiber 101.

A disadvantage of the device of FIG. 2 lies in the relatively large dimensions of connector 113, particularly due to the presence of O-ring 207 surrounding input surface 101a of optical fiber 101. It is further difficult to guarantee a fine contact between the fiber and the window. Further, problems of light reflection, particularly directly on the laser itself, may arise in case of a poor index matching. This may cause an instability of the laser and cause a failure thereof.

Figure 3A:
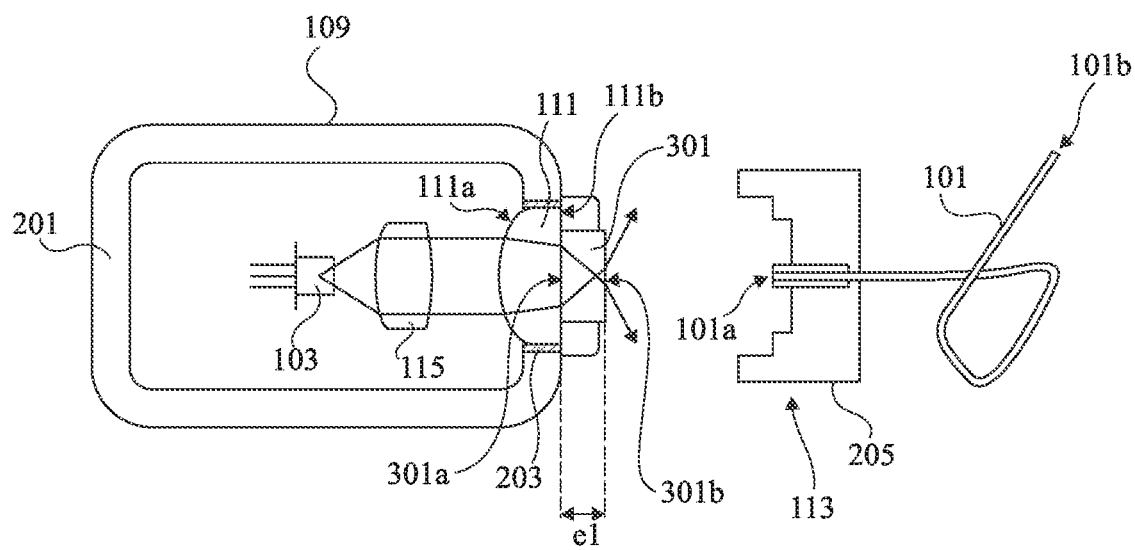
FIGS. 3A and 3B are cross-section views illustrating an example of an embodiment of an implantable device for the optical irradiation of the brain.
Figure 3B:
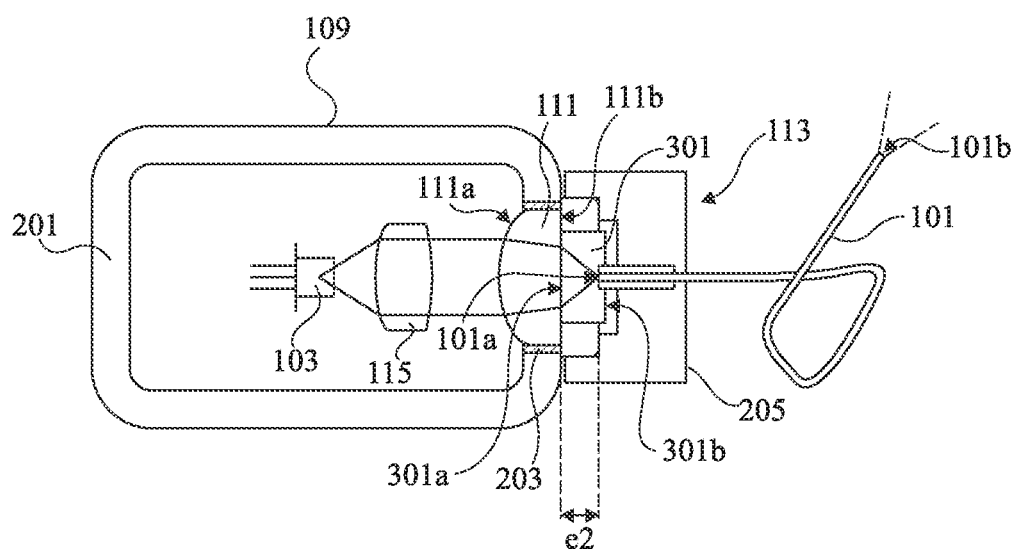

FIGS. 3A and 3B are cross-section views illustrating an embodiment of an implantable device for the optical irradiation of the brain. The device of FIGS. 3A and 3B comprises many elements common with the device of FIGS. 1 and 2. These elements will thus not be described again in detail hereafter. Hereafter, only the differences with the device of FIGS. 1 and 2 will be highlighted.

As in the example of FIG. 2, the device of FIGS. 3A and 3B comprises an optical fiber 101, a light source 103, a package 109 for protecting light source 103 provided with a transparent window 111, an optical system 115 for shaping the light emitted by source 103, and a connector 113 capable of connecting optical fiber 101 to package 109 to achieve an optical coupling between light source 103 and optical fiber 101 via window 111.

FIG. 3A shows the device in disconnected position, that is, when connector 113 is disconnected from package 109, there then being no coupling between optical fiber 101 and light source 103. FIG. 3B shows the device in connected position, that is, when connector 113 is connected to package 109, optical fiber 101 then being optically coupled to light source 103. In the same way as in FIG. 2, the elements for locking connector 113 in connected position and for unlocking it have not been shown in FIGS. 3A and 3B.

The device of FIGS. 3A and 3B differs from the device of FIG. 2 in that it comprises no O-ring around input surface 101a of optical fiber 101, between body 205 of connector 113 and package 109.

The device of FIGS. 3A and 3B however comprises an interface element 301 made of a transparent elastomeric material capable of being maintained pressed or compressed between output surface 111b of window 111 and input surface 101a of optical fiber 101 when connector 113 is connected to package 109. Interface element 301 is for example a plate or a disk. As an example, interface element 301 is made of a material having a Young's modulus in the range from 1 to 100 MPa. Interface element 301 is for example made of a biocompatible material. As an example, interface element 301 is made of silicone or of polyurethane. Interface element 301 comprises a first surface or input surface 301a, in contact with output surface 111b of window 111 when connector 113 is connected to package 109. Interface element 301 further comprises a second surface or output surface 301b opposite to surface 301a, in contact with input surface 101a of optical fiber 101 when connector 113 is connected to package 109. Surfaces 301a and 301b of element 301 are for example substantially planar and parallel to each other. Interface element 301 is for example solid with package 109 in the disconnected state. As an example, interface element 301 may be inserted in place opposite window 111 in a housing of package 109 provided for this purpose. As a variation, element 301 may be solid with connector 113 in the disconnected state. As a variation, element 301 may be an independent removable part, that is, affixed neither to connector 113 nor to package 109 in the disconnected state.

In the disconnected position (FIG. 3A), element 301 has a first thickness (or distance between its surfaces 301a and 301b) e1 at the level of its region of coupling with optical fiber 101, that is, opposite the portion of its surface 301b intended to be placed in contact with input surface 101a of optical fiber 101 during the connection of connector 113 to the package. As an example, thickness e1 is in the range from 0.5 to 2 mm.

In connected position (FIG. 3B), thickness e2 of element 301 opposite input surface 101a of optical fiber 101 is smaller than thickness e1. As an example, thickness e1 of element 301 in disconnected position is in the range from 1.1 to 1.3 times thickness e2 of element 301 in connected position. In practice, connector 113 and/or package 109 may define a vent or housing capable of containing the excess material at the periphery of the area of coupling with optical fiber 101, in the case where element 301 is made of a non-compressible or little compressible material.

In the device of FIGS. 3A and 3B, the optical assembly comprising optical system 115, window 111, and interface element 301 is capable of focusing the light generated by source 103 outside of package 109, at a distance from output surface 111b of window 111 substantially equal to thickness e2 of interface element 301 in connected position. Thus, in connected position, the light generated by source 103 is focused substantially onto input surface 101a of optical fiber 101, and conducted by optical fiber 101 to its output surface 101b. It should be noted that although window 111 has been shown with a convex input surface 111b in the example of FIGS. 3A and 3B, the described embodiments are not limited to this specific case. As a variation, window 111 may have a planar input surface 111a substantially parallel to its output surface 111b, or a concave input surface 111a.

Due to its resilient properties, and due to its being maintained compressed between window 111 and optical fiber 101, interface element 301 forms a seal preventing, in connected position, unwanted substances from interposing between output surface 111b of window 111 and input surface 101a of optical fiber 101. It is then not necessary to provide an O-ring around input surface 101a of optical fiber 101, which enables to decrease the dimensions of connector 113 with respect to a system of the type described in relation with FIG. 2.

Another advantage of the device of FIGS. 3A and 3B is that interface element 301b enables to decrease reflection losses and/or parasitic phenomena of backscattering of light on source 103, which are particularly problematic in the case of a laser source. As an example, interface element 301 is made of a material having an optical index substantially equal to that of the material of input surface 101a of optical fiber 101, or of a material having an optical index intermediate between that of the material of window 111 and that of the material of input surface 101a of optical fiber 101. Parasitic reflections of light on input surface 101a of the optical fiber are thus decreased with respect to a device of the type described in relation with FIG. 2. In the device of FIGS. 3A and 3B, parasitic reflections may occur on input surface 301a of interface element 301. Such reflections are however less disturbing since they occur outside of the focal plane of the optical system.

It should further be noted that in the device of FIGS. 3A and 3B, due to the resilient properties of interface element 301, the tolerance margin for the positioning of input surface 101a of optical fiber 101 along the axis of source 103 is greater than that of a system of the type described in relation with FIG. 2, where the rigid window is directly placed in contact with input surface 101a of optical fiber 101 (a spring mechanism should then in practice be provided to maintain input surface 101a of optical fiber 101 pressed against the output surface 111b of window 111, with a holding force selected independently from the force of crushing of O-ring 207). This enables to simplify connector 113 as compared with a device of the type described in relation with FIG. 2.

Figure 4:
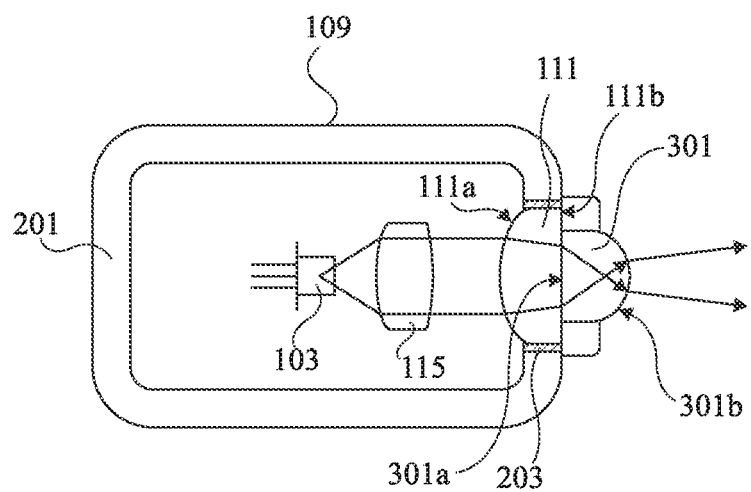
FIG. 4 is a cross-section view illustrating an alternative embodiment of the device of FIGS. 3A and 3B.

FIG. 4 is a cross-section view illustrating an alternative embodiment of the device of FIGS. 3A and 3B. The device of FIG. 4 differs from the device of FIGS. 3A and 3B essentially in that, in the example of FIG. 4, output surface 301b of interface element 301 is not planar, but has a bulged or convex surface, which enables to limit risks of trapping a possible air bubble between output surface 301b of element 301 and input surface 301b of element 301 and input surface 101a of optical fiber 101 on connection of connector 113 to package 109. In connected position, due to the crashing of element 301, the surface of element 301 in contact with input surface 101a of optical fiber 101 becomes substantially planar and parallel to input surface 301a of interface element 301 again.

Figure 5:
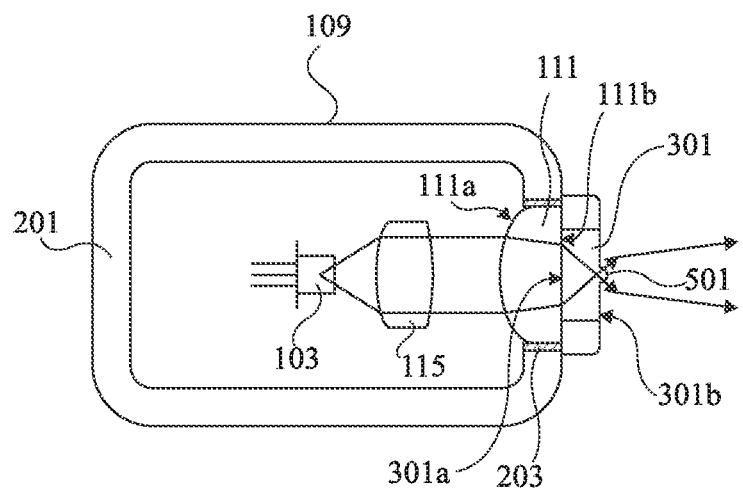
FIG. 5 is a cross-section view illustrating another alternative embodiment of the device of FIGS. 3A and 3B.

FIG. 5 is a cross-section view illustrating another alternative embodiment of the device of FIGS. 3A and 3B. The device of FIG. 5 differs from the device of FIG. 4 essentially in that, in the example of FIG. 5, output surface 301b of interface element 301 is not bulged on its entire surface, but has a bulged excrescence 501 in a central portion intended to be placed in contact with input surface 101a of optical fiber 101. The peripheral portion of output surface 301b of interface element 301 is substantially parallel to input surface 301a of element 301. As in the example of FIG. 4, the provision of a bulged portion on surface 301b of element 301 enables to limit risks of trapping a possible air bubble between surface 301b of element 301 and input surface 101a of optical fiber 101 on connection of connector 113 to package 109. In connected position, due to the crushing of element 301, the surface of element 301 in contact with input surface 101*a* of optical fiber 101 becomes substantially planar and parallel to input surface 301*a* of interface element 301 again.

In another alternative embodiment (not shown), input surface 101*a* of optical fiber 101 is not orthogonal to the main propagation axis of light, but has an inclination, for example, in the range from 8 to 12 degrees, relative to this axis, to reject the beam outside of the laser coupling angle.

Figure 6:
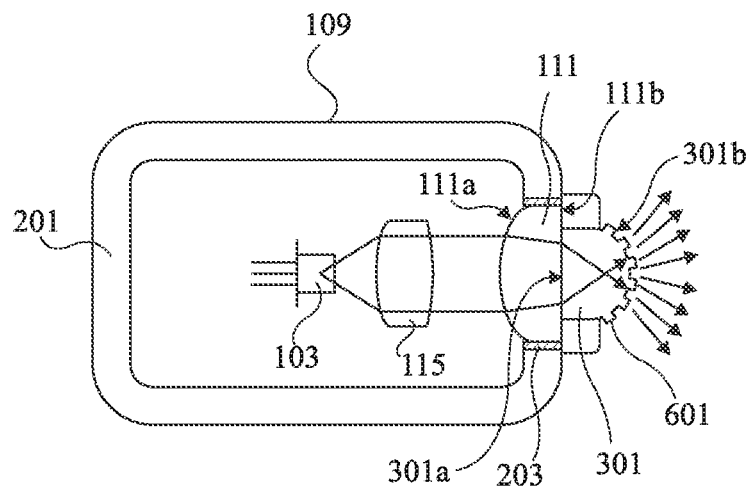
FIG. 6 is a cross-section view illustrating another alternative embodiment of the device of FIGS. 3A and 3B.

FIG. 6 is a cross-section view illustrating another alternative embodiment of the device of FIGS. 3A and 3B. The device of FIG. 6 differs from the device of FIG. 4 essentially in that, in the example of FIG. 6, output surface 301*b* of interface element 301 is not smooth, but has nanostructures or microstructures 601, for example, structures having dimensions in the range from 200 nm to 200 µm, over all or part of its surface. In disconnected position, structures 601 diffract the light beam, which decreases risks of dazzling or of burns for an operator handling the device, particularly when source 103 is a laser source. In connected position, due to the crushing of element 301, the surface of element 301 in contact with input surface 101*a* of optical fiber 101 becomes smooth again. Although FIG. 6 has been shown with an interface element 301 having an output surface 301*b* having a bulged general shape (similar to that of the device of FIG. 4), the variation of FIG. 6 may be implemented whatever the general shape of output surface 301*b* of interface element 301.

Specific embodiments have been described. Various alterations, modifications, and improvements will occur to those skilled in the art. In particular, the described embodiments are not limited to the above-described example of application to an implantable medical device. More generally, the provided solution may have applications in other fields where it is desired to couple a light source to an optical fiber while protecting the optical coupling interface between the light source and the optical fiber against impurities. The selection of the materials may particularly be adapted accordingly.

What is claimed is:

1. A device comprising:
   a light source assembled in a package, the package comprising a transparent window opposite the light source;
   an optical fiber fitted with a connector capable of detachably engaging with the package to maintain an input surface of the optical fiber opposite the light source and the window, wherein the input surface is an end of the optical fiber; and
   an interface element made of a transparent elastomeric material capable, in connected position, of being maintained compressed between the window and the input surface of the optical fiber
   wherein, in disconnected position, the surface of the interface element intended to be placed in contact with the input surface of the optical fiber has nanostructures or microstructures adapted to diffract light emitted by the light source, thereby decreasing risks of dazzling or of burns for an operator handling the device,
   and wherein, in a connected position, the surface of the interface element placed in contact with the input surface of the optical fiber is smooth.

2. The device of claim 1, wherein, opposite a region where it is placed in contact with the input surface of the optical fiber, the interface element has a first thickness in disconnected position and a second thickness in connected position, the first thickness being from 1.1 to 1.3 times greater than the second thickness.

3. The device of claim 1, wherein, in disconnected position, the surface of the interface element intended to be placed in contact with the input surface of the optical fiber is bulged.

4. The device of claim 1, wherein the interface element is made of silicone or of polyurethane.

5. The device of claim 1, wherein the light source is a laser source.

6. The device of claim 1, wherein the window is made of sapphire or of silica.

7. The device of claim 1, wherein the package is hermetically closed.

8. The device of claim 1, further comprising an optical system capable, in connected position, of focusing the light emitted by the source onto the input surface of the optical fiber.

9. The device of 1, wherein the interface element is rigidly assembled to the package or to the connector.

10. The device of claim 1, further comprising a power supply and control unit coupled to the light source by a connecting cable.

* * * * *